United States Patent [19]

Palumbo et al.

[11] Patent Number: 5,482,761
[45] Date of Patent: Jan. 9, 1996

[54] LAYERED, ABSORBENT STRUCTURE

[75] Inventors: Gianfranco Palumbo, Pescara; Giovanni Carlucci, Chieti, both of Italy

[73] Assignee: The Procter & Gamble Company, Cincinnati, Ohio

[21] Appl. No.: 360,765
[22] PCT Filed: Jun. 25, 1993
[86] PCT No.: PCT/US93/06128
§ 371 Date: Apr. 17, 1995
§ 102(e) Date: Apr. 17, 1995
[87] PCT Pub. No.: WO94/01069
PCT Pub. Date: Jan. 20, 1994

[30] Foreign Application Priority Data

Jul. 3, 1992 [IT] Italy ................... TO92A0566

[51] Int. Cl.[6] ...................... A61F 13/16; B32B 3/00
[52] U.S. Cl. ................ 428/198; 428/201; 428/206; 428/283; 428/323; 428/913; 264/126
[58] Field of Search ....................... 428/198, 201, 428/206, 283, 323, 913; 264/126

[56] References Cited

U.S. PATENT DOCUMENTS

| 3,870,592 | 3/1975 | Brock et al. | |
| 4,318,408 | 3/1982 | Korpman | 128/287 |
| 4,578,068 | 3/1986 | Kramer et al. | 604/368 |
| 4,685,909 | 8/1995 | Berg et al. | 604/360 |

FOREIGN PATENT DOCUMENTS

WO95/03019  2/1995  WIPO.

Primary Examiner—Patrick J. Ryan
Assistant Examiner—Richard Weisberger
Attorney, Agent, or Firm—Jacobus C. Rasser; E. Kelly Linman

[57] ABSTRACT

A thin, layered, absorbent structure comprises first and second layers of fibrous material and an intermediate layer comprising particles of a hydrogelling, absorbent material and particles of a thermoplastic, polymeric, organic material, the first and second fibrous layers extend beyond the intermediate layer laterally to form longitudinal edge portions.

The two fibrous layers are bound together with the intermediate layer between them by the melting of the particles of thermoplastic, polymeric, organic material and by means of a continuous line of adhesive extending longitudinally on each longitudinal edge portion.

24 Claims, 1 Drawing Sheet

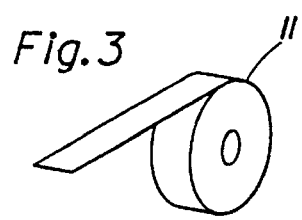
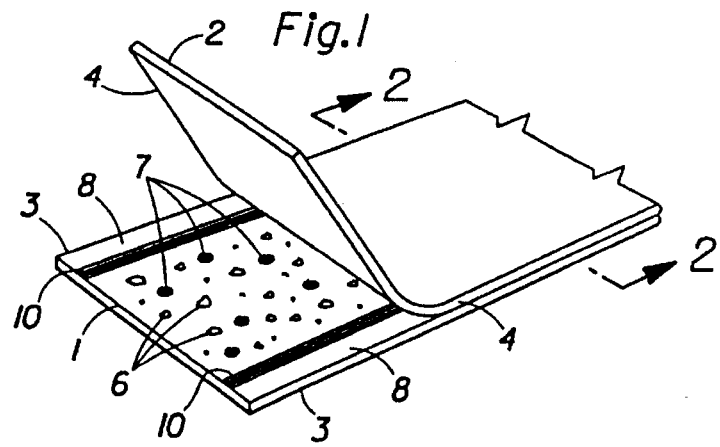
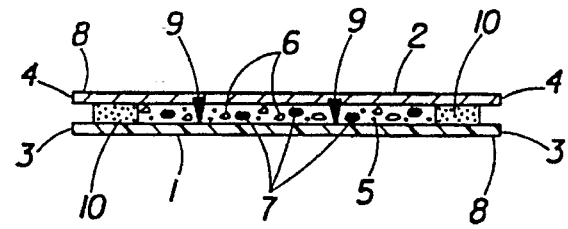
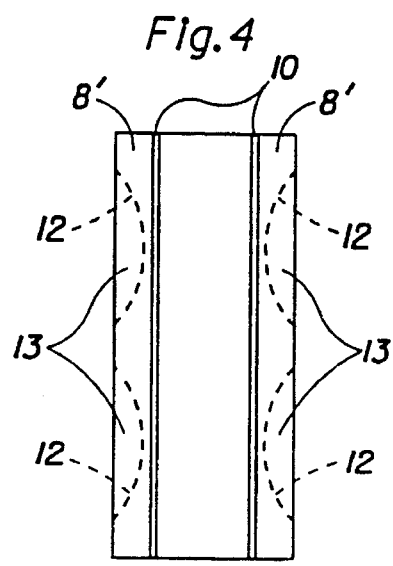
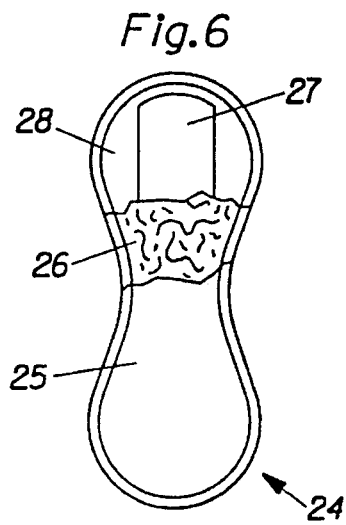
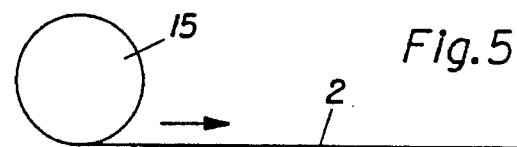
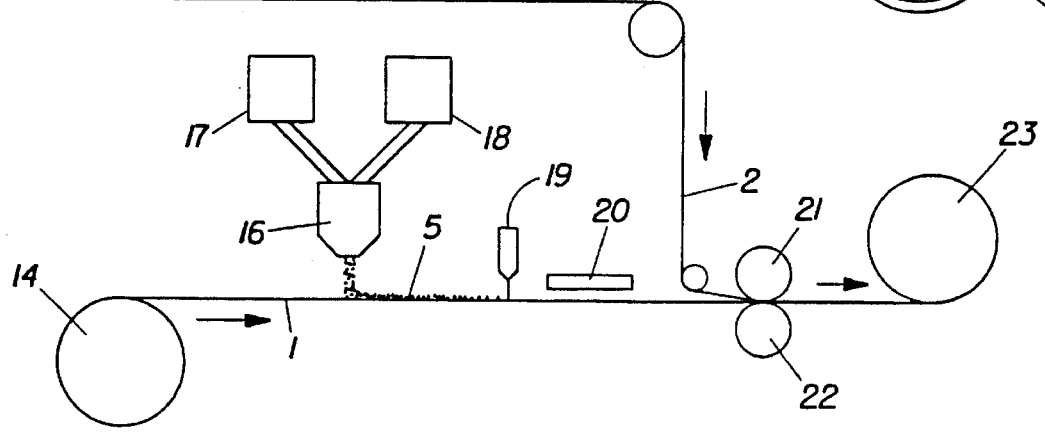

LAYERED, ABSORBENT STRUCTURE

The present invention relates to layered, absorbent structures constituted by fibrous layers with particles of hydrogelling absorbent material.

The structures may be used as absorbent elements in disposable absorbent articles such as sanitary towels, dressings, babies' nappies and the like.

Disposable absorbent articles are well known and all have absorbent elements for absorbing and retaining body fluids; an absorbent element must be able to acquire liquid rapidly and to distribute it internally so as to prevent leakages and must also have a good capacity to retain the fluids when subjected to the normal pressures of use.

Absorbent elements made mainly of hydrophilic fibrous material such as, for example, pads of cellulose fibres, layers of wadding, or the like generally have satisfactory characteristics as regards their liquid-absorption rate and can distribute the liquid effectively within them but are very ineffective from the point of view of retention when subjected to the normal pressures of use.

The use of hydrogelling absorbent materials in combination with hydrophilic fibres in order to increase the absorption and retention capacities of the absorbent elements is known.

Hydrogelling absorbent materials, commonly known as superabsorbents, are polymers which can swell up and absorb large quantities of liquid, particularly water, or also, to a lesser extent, body fluids.

They also have the particular property that they retain the fluids even under moderate pressure; owing to this characteristic, their use in absorbent elements for disposable absorbent articles has been proposed for some time.

The high absorption capacity of superabsorbents is not, however, combined with similarly rapid absorption and this may adversely affect the performance of absorbent articles incorporating these substances.

In fact, superabsorbents may give rise to a phenomenon defined as "gel blocking"; when a particle of superabsorbent is in contact with the liquid, its external surface starts to absorb the liquid and swells up obstructing the transmission of the liquid into the particle itself; the liquid can penetrate further into the still-dry core of the particle only by means of a very slow diffusion mechanism.

This phenomenon may prevent full use being made of the large absorption capacities of superabsorbent substances.

Leaving out of consideration the type of superabsorbent material and the shapes and sizes of the particles, "gel blocking" is generally encouraged by the formation of agglomerations of superabsorbent particles within the absorbent structure, which may occur either before use, when the particles are still dry, or during use, when the particles start to absorb the liquid and swell up.

In any case, with the use of hydrogelling absorbent materials, it is possible to produce absorbent elements which contain less hydrophilic fibres for a given absorption capacity and which consequently have smaller dimensions, particularly widths, than conventional absorbent elements made of fibres alone.

Structures have been formed in which the fibres and the particles of hydrogelling, absorbent material are disposed in separate, generally very thin, superposed layers.

Many particular forms of layered, absorbent structures of this type, in which the fibrous material is represented by one of more layers of wadding, absorbent paper or non-woven fabric, and in which the particles of hydrogelling absorbent material are incorporated in the structure in various ways, are known in the art.

In layered structures which are formed dry, the at least two fibrous layers are bound together solely by the intertwining of fibres and the particles of hydrogelling absorbent material between them are held in position by the two fibrous layers joined together; a better connection between the fibrous layers can be achieved by subjecting the structure to an embossing process which encourages the fibres to intertwine by causing slight relative slippage between the layers; a solution of this type is described, for example, in U.S. Pat. No. 4,578,068.

Alternatively, the layered structure may be formed damp by the application of water, or preferably steam, and pressure; the connection between the fibrous layers is achieved mainly by virtue of the particles of hydrogelling, absorbent material which become sticky and act as an adhesive between the fibrous layers.

In neither case is the structure very stable and the fibrous layers may separate, for example, along their edges, leaving the particles of hydrogelling absorbent material free to slide between the surfaces of the layers between which they are included; the particles of hydrogelling absorbent material may thus become concentrated locally thereby encouraging, and possibly aggravating, the establishment of the "gel blocking" phenomenon in use, and may also escape from the edges of the structure, in any case reducing the absorption capacity of the structure.

Another solution for the formation of a layered absorbent structure provides for the use of an adhesive, for example, of the hot melting type, applied to the surface of one of the fibrous layers with the dual purpose of bonding the two fibrous layers together and simultaneously fixing the particles of superabsorbent material between them.

The use of an adhesive may, however, affect the absorption characteristics both of the fibrous layer to which the adhesive is applied, and of the superabsorbent particles which come into contact with the adhesive.

In general, therefore, it is necessary not to use an excessive quantity of adhesive and consequently not to eliminate completely the possibility of the loss of superabsorbent material from the edges of the layered structure.

For this reason, layered absorbent structures of the type described are formed directly on the production line for the absorbent articles in which they are to be incorporated, since it is not convenient to produce them independently as semi-finished products.

The problem of the loss of hydrogelling absorbent material along the edges is common to all the layered structures described up to now and has been solved in various ways in known products; for example, by surrounding the structure completely with a layer of wadding, which involves the addition of a further element, or by the use of a single layer of fibrous material on which the adhesive and the superabsorbent material are distributed only on a central longitudinal strip and subsequently folding the two side portions so that they partially overlap approximately on the longitudinal axis.

This solution solves the problem of the loss of hydrogelling absorbent material from the edges of the structure without requiring the presence of additional elements but does not allow different materials to be used for the two fibrous layers. Moreover, it involves the use of a larger quantity of material than would be needed simply to superpose two layers of the same width as the finished product.

There remains therefore the problem of providing a thin, layered, absorbent structure which does not have the disadvantages described above connected with the method of joining together the various layers of which it is made up and, preferably, of reducing the quantity of material so as to produce a thinner and lighter structure.

The object of the present invention is to improve the absorption and stability characteristics of thin, layered, absorbent structures containing hydrogelling, absorbent material for use in disposable absorbent articles.

According to the present invention, this object is achieved by virtue of a thin, layered, absorbent structure having the specific characteristics recited in the following claims.

Further subjects of the invention are an article comprising the structure as well as a method for the manufacture thereof.

In summary, the invention relates to a thin, layered, absorbent structure formed by at least two fibrous layers comprising between them a layer of particles of hydrogelling, absorbent material, the two fibrous layers being joined together by particles of thermoplastic, polymeric, organic material distributed and mixed with the hydrogelling, absorbent material, and by two lines of adhesive disposed along the longitudinal edges of the structure.

Further characteristics and advantages of the invention will become clear from the description which follows, given purely by way of non-limiting example, with reference to the appended drawings, in which:

FIG. 1 is a perspective view of a thin, layered, absorbent structure formed according to the present invention, with one of the two layers partially raised, FIG. 2 is a sectional view of the thin, layered, absorbent structure, taken on the line II—II of FIG. 1, FIG. 3 is a perspective view of a continuous strip of the thin, layered, absorbent structure of the present invention rolled in the form of a roll, FIG. 4 is a plan view of a continuous strip of an alternative configuration of the thin, layered, absorbent structure, FIG. 5 is a schematic view of a device for producing a thin, layered, absorbent structure according to the present invention, and FIG. 6 is a plan view of a disposable sanitary towel using a thin, layered, absorbent structure according to the present invention as an absorbent element.

The thin, layered, absorbent structures of the present invention will be described herein in relation to their use in disposable absorbent articles; the articles are worn by the user in direct contact with the body; their purpose is to absorb body fluids and they are then thrown away after a single use.

FIGS. 1 and 2 show a preferred configuration of a thin, layered, absorbent structure formed according to the present invention. In FIG. 2, one of the layers is partially raised to show its construction more clearly.

In FIG. 1 it is possible to distinguish a first fibrous layer 1 and a second fibrous layer 2 in the form of two continuous strips of the same width, which are superposed so that their respective longitudinal edges 3 and 4 coincide; the fibrous layers may be made of various materials such as, for example, paper, wadding, or non-woven fabric; they are preferably made of dry-formed layers, generally referred to as "air laid" layers in English, of short cellulose fibres having a basic weight of between 20 g/m² and 150 g/m².

Between the two fibrous layers 1 and 2 there is an intermediate layer 5 made of a mixture of particles of hydrogelling, absorbent material 6 and particles of a thermoplastic, polymeric, organic material 7; the width of the intermediate layer 5 is less than the widths of the two outer fibrous layers 1 and 2 which extend beyond the intermediate layer 5 laterally forming two longitudinal edge portions 8 at their respective longitudinal edges 3 and 4.

The two outer fibrous layers 1 and 2 are bonded together in the central region in which the intermediate layer 5 is present by the application of heat and moderate pressure to melt the particles 7 of thermoplastic, polymeric, organic material present in the intermediate layer 5, mixed with the particles 6 of hydrogelling, absorbent material. As can best be seen in FIG. 2, which is a section of the absorbent structure taken on the line AA' of FIG. 1, the bond between the fibrous layers 1 and 2 is formed at discrete spaced-apart points 9 generated by the melting of the individual particles 7 of hot melting, polymeric, organic material; as it melts, the polymeric material bonds the fibres of the two adjacent layers 1 and 2 together.

In practice, the particles 6 of hydrogelling, absorbent material are affected only to a very marginal extent by the melting of the particles 7 of hot melting, polymeric, organic material, and thus remain trapped between the two fibrous layers without being substantially bonded thereto, being only minimally affected by the presence of any non-absorbent material directly in contact with them.

Moreover, the overall surface areas of the bond points represent a small fraction of the surface areas of the fibrous layers 1 and 2 the absorption characteristics of which thus remain almost unchanged.

Two continuous lines 10 of adhesive are also applied to the two sides of the intermediate layer 5 on the longitudinal edge regions 8 of the two outer fibrous layers 1 and 2 so as to eliminate any further possibility of particles of hydrogelling, absorbent material 6 escaping from the longitudinal edges of the layered structure, which correspond to the superposed edges 3 and 4 of the two fibrous layers, and also reinforcing the connection between the fibrous layers themselves.

The hydrogelling material, which is preferably distributed in the form of particles 6, may be made of inorganic or organic substances such as cross-linked polymers, all known from the prior art.

The average dimensions of the particles 6, given as a weighted average of the smallest dimensions of the individual particles, may be between 100 microns and 800 microns.

The quantity of the hydrogelling absorbent material 6 distributed to form the intermediate layer 5, together with the thermoplastic polymeric organic material 7, may be between 30 g/m² and 150 g/m².

The finely-divided, thermoplastic, polymeric, organic material has the purpose of bonding the two fibrous layers 1 and 2 together by melting and forming discrete, spaced-apart bond points 9 between the fibres of the two layers.

For this purpose, the quantity of thermoplastic, polymeric, organic material distributed and mixed with the hydrogelling, absorbent material is between 5 g/m² and 30 g/m².

The thermoplastic, polymeric, organic material can preferably be melted at a temperature such as not to interfere with the characteristics of the other components of the layered structure, particularly the fibrous layers and the hydrogelling, absorbent material; moreover, it must have fluidity characteristics such as to enable the bond between the fibres to be formed rapidly; in other words, when it melts, the individual particle of thermoplastic polymeric organic material is interpenetrated by fibres belonging to both the fibrous layers and when it subsequently sets, it forms a single bond point between the two layers 1 and 2.

It has been found that these preferred characteristics can be achieved by a thermoplastic, polymeric, organic material 7 having a melt flow index (M.F.I.), evaluated by the ASTM method D 1238-85 under conditions 190/2.16, of at least 25 g/10 min., preferably at least 40 g/10 min, and even more preferably at least 60 g/10 min.

If the layers 1 and 2 are made of an air-laid short cellulose fibre material, it has been found particularly preferable to use a thermoplastic, polymeric, organic material composed of particles of high-density polyethylene with maximum dimensions of about 400 microns, characterised by a melt flow index of about 50 g/10 min., of which the quantity distributed is between 5 g/m$^2$ and 15 g/m$^2$.

Surprisingly, it has been found that the apparent contradiction due to the incompatibility of polyethylene, which is typically hydrophobic, and cellulose fibres is in fact translated into an advantage; in fact, it may be assumed that, during the heating of the structure, the melted polyethylene particles can rapidly incorporate the cellulose fibres belonging to the two adjacent layers by virtue of the desired characteristics expressed in terms of the melt flow index, but does not interpenetrate the fibrous mass further, and thus creates discrete and well-defined bond points between the layers, any effect of the polyethylene on the characteristics of the structure in terms, for example, of its absorption capacity, being limited to a maximum extent.

The thin, layered, absorbent structure of the present invention may also be formed from two different fibrous layers or may comprise more than two fibrous layers, and consequently more than one intermediate layer formed by the mixture of particles of hydrogelling, absorbent material and particles of thermoplastic, polymeric, organic material.

In any case, by virtue also of the continuous lines of adhesive disposed between the fibrous layers on the respective longitudinal edge portions which prevent the particulate material forming the intermediate layer from escaping from the longitudinal edges of the structure, the structure has the further advantage than it can be produced separately and stored as it is, for example, as a continuous strip rolled in the form of a roll 1, shown in FIG. 3, which can subsequently be used on the production line for disposable absorbent articles, for example, sanitary towels, which incorporate the structure as an absorbent element.

In an alternative configuration, shown in FIG. 4, the thin, layered, absorbent structure of the present invention comprises longitudinal edge portions 8' which are particularly wide and extend laterally beyond the continuous lines of adhesive 10; the thin, layered, absorbent structure can thus be incorporated in a shaped absorbent article and can be shaped itself, for example, along cutting lines indicated 12, without involving the need to discard the material constituting the intermediate layer along with the scraps 13 formed from the superposed fibrous layers.

FIG. 5 is a simplified diagram of a method of producing a thin, layered, absorbent structure according to the present invention.

The reels 14, 15 supply the first and second fibrous layers 1 and 2, which may be of the same material or of different materials, in the form of respective continuous strips; the mixer/dispenser 16, which is supplied by the container 17 of hydrogelling, absorbent material and by the container 18 of thermoplastic, polymeric, organic material, forms the intermediate layer 5 on the surface of the first fibrous layer 1; the two extruders 19, only one of which is visible in FIG. 5, then form the two continuous lines 10 of adhesive, for example, of the hot melting type, at the two sides of the intermediate layer 5 and on the longitudinal edge portions of the first fibrous layer 1.

The first fibrous layer 1 and the intermediate layer 5 are heated to melt the particles of polymeric, organic material 7, for example, by means of a radiant heating element 20; the second fibrous layer 2 is then superposed on the first fibrous layer 1 and on the intermediate layer 5 and the three layers, combined to form the structure, are bonded by subjecting the structure to moderate pressure by passing it between the two rollers 21 and 22 bringing about the adhesion of the two fibrous layers 1 and 2 by means of the melted particles of polymeric, organic material 7 and the two continuous lines of adhesive 10. The outer surface of at least one of the two rollers 21 and 22 is preferably made resilient by being covered with a layer, for example, of silicone rubber.

Finally, the thin, layered, absorbent structure is collected on the reel 23 in the form of a continuous strip.

A disposable sanitary towel 24, shown in FIG. 6, which uses a thin, layered, absorbent structure formed according to the present invention, will be described by way of non-limiting example.

The towel 24 is of the shaped type and is constituted by an upper liquid-permeable layer 25 made of a perforated polyethylene film 0.350 mm thick and 24.0 g/m$^2$ weight, a substrate 26 formed by a non-woven fabric of carded rayon (67%) and polyester (33%) fibres intertwined by means of water jets, 0.700 mm thick and 50 g/m$^2$ weight, an absorbent element 27 formed by a thin, layered, absorbent structure according to the present invention, and a lower layer 28 which is impermeable to liquids, formed by a polyethylene film 0.025 mm thick and 24.0 g/m$^2$ weight.

The absorbent element 27, which is substantially rectangular with rounded ends, is 220 mm long and 65 mm wide with an overall thickness of 1.030 mm and a weight of 176.0 g/m$^2$.

The thin, layered, absorbent structure which constitutes the absorbent element 27 is composed of two outer dry-formed ("air laid") short cellulose fibre layers, each with a weight of 55 g/m$^2$ and an intermediate layer of particles of a hydrogelling, absorbent material constituted by a polyacrylate in granules with average dimensions of between 300 microns and 500 microns, of which the quantity distributed is about 50 g/m$^2$, and particles of a thermoplastic polymeric, organic material constituted by high-density polyethylene in particles with maximum dimensions of about 400 microns, having an M.F.I. of about 50 g/10 min, of which the quantity distributed is about 10 g/m$^2$. The two continuous lines of adhesive are constituted by two lines of hot melting adhesive about 2 mm wide.

The thin, layered, absorbent structure incorporated in the sanitary towel performed well in restricted use tests both from the point of view of its capacity to absorb and retain liquid and from the point of view of the stability of the elements which make it up.

Naturally, the principle of the invention remaining the same, the details of construction may be varied widely from those described and illustrated without thereby departing from the scope of the present invention. In particular, there may be more than two layers of fibrous material thus forming several pairs of fibrous layers each enclosing an intermediate layer comprising a mixture of hydrogelling, absorbent material and thermoplastic material for joining the fibrous layers together in the manner described above.

What is claimed is:

1. A layered, absorbent structure, characterized in that it comprises, in combination, first and second layers (1, 2) of fibrous material and an intermediate layer (5) comprising a hydrogelling, absorbent material (3) distributed between the first and second fibrous layers (1, 2), at least one of the first and second layers (1, 2) being permeable to liquids, and the intermediate layer (5) also comprising a thermoplastic material (7) which bonds at least the first and second fibrous layers (1, 2) together, with the intermediate layer (5) between them, forming discrete, spaced-apart bond points (9).

2. An absorbent structure according to claim 1, characterized in that the first and second layers (1, 2) of fibrous material extend beyond the intermediate layer (5) laterally forming longitudinal edge portions (8), and in that the first and second layers (1, 2) of fibrous material are bonded together along each of the edge portions (8) by means of a preferably continuous line of adhesive (10).

3. An absorbent structure according to claim 1, characterized in that the first and second layers (1, 2) of fibrous material have a basic weight of between about 20 g/m$^2$ and about 150 g/m$^2$.

4. An absorbent structure according to claim 1, characterized in that the quantity of the hydrogelling, absorbent material (6) distributed between the first and second fibrous layers (1, 2) is between about 30 g/m$^2$ and about 150 g/m$^2$.

5. An absorbent structure according to claim 1, characterized in that the thermoplastic material (7) is a polymeric, organic material.

6. An absorbent structure according to claim 1, characterized in that the quantity of thermoplastic material (7) present is between about 5 g/m$^2$ and about 30 g/m$^2$.

7. An absorbent structure according to claim 1, characterized in that the thermoplastic material (7) is present in the form of finely divided material.

8. An absorbent structure according to claim 1, characterized in that the thermoplastic material (7) has a melt flow index (M.F.I.) of at least 25 g/10 min.

9. A layered, absorbent structure, characterized in that it comprises, in combination, first and second layers (1, 2) of a fibrous material with a basic weight of between about 20 g/m$^2$ and about 150 g/m$^2$, as well as an intermediate layer (5) comprising particles of a hydrogelling, absorbent material of which a quantity of between about 30 g/m$^2$ and about 150 g/m$^2$ is distributed between the first and second fibrous layers (1, 2), at least one of the first and second fibrous layers (1, 2) being permeable to liquids, the first and second fibrous layers (1, 2) extending beyond the intermediate layer (5) laterally to form longitudinal edge portions (8), the intermediate layer (5) comprising a mixture of hydrogelling, absorbent material (6) and a quantity of between about 5 g/m$^2$ and about 30 g/m$^2$ of a finely divided thermoplastic, polymeric, organic material (7), which has a melt flow index (M.F.I.) of at least 25 g/10 min. and is intended to fond at least the first and second fibrous layers (1, 2) together with the intermediate layer (5) between them, forming discrete, spaced-apart bond spots (9), the layered, absorbent structure also being characterized in that the layers of fibrous material (1, 2) are bonded together along each longitudinal edge portion (8) by means of a continuous line of adhesive (10).

10. An absorbent structure according to claim 1, characterized in that it is generally rectangular.

11. An absorbent structure according to claim 1, characterized in that it comprises more than two layers of fibrous material with an intermediate layer (5) between each pair of fibrous layers, the intermediate layer comprising a mixture of hydrogelling absorbent material (6) and finely divided, thermoplastic material (7).

12. An absorbent structure according to claim 1, characterized in that the layers of fibrous material (1, 2) comprise dry-formed layers of short cellulose fibres.

13. An absorbent structure according to claim 1, characterized in that the layers of fibrous material (1, 2) are made of different materials.

14. An absorbent structure according to claim 1, characterized in that the thermoplastic material (7) has a melt flow index of at least 40 g/10 min., preferably at least 60 g/10 min.

15. An absorbent structure according to claim 1, characterized in that the thermoplastic material (7) is in the form of solid hot melting particles.

16. An absorbent structure according to claim 1, characterised in that the thermoplastic material is polyethylene-based.

17. An absorbent structure according to claim 1, characterised in that the thermoplastic material is in the form of a quantity of between about 5 g/m$^2$ and 15 g/m$^2$ of polyethylene particles with maximum dimensions of 400 microns.

18. An absorbent structure according to claim 9, characterised in that the adhesion lines (10) comprise a hot melting adhesive.

19. An absorbent structure according to claim 1, characterised in that its thickness is no more than 3 mm.

20. A disposable, absorbent article comprising an absorbent structure according to claim 9, disposed between an upper liquid-permeable layer (15) and a lower layer (28) which is impermeable to liquids.

21. A disposable, absorbent article according to claim 20 in the form of a sanitary towel with a thickness no greater than about 4 mm.

22. A method of producing an absorbent structure according to claim 1, characterized in that it comprises the following steps:

providing the first layer (1) of fibrous material, providing the second layer (2) of fibrous material of a width such that it can contact the first layer (1) along respective longitudinal edge portions (8), distributing a mixture of particles of hydrogelling, absorbent material (6) as well as the finely divided, thermoplastic material (7) on the first layer (1) of fibrous material, the mixture being distributed in a manner such that the longitudinal edge portions (8) of the first layer (1) are left free, applying lines of adhesive (10) to the longitudinal edge portions of the first layer (1), and combining the first layer (1), the intermediate layer (5) and the second layer (2) in a layered structure by the application of heat and pressure to melt the thermoplastic material so as to form discrete, spaced-apart bond points (9) between the first layer (1) and the second layer (2) with the lines of adhesive (10) bonding the first and second layers (1, 2) together along the longitudinal edge portions (8).

23. A method according to claim 22, characterised in that the lines of adhesive (10) are applied in the form of continuous lines.

24. A method of producing an absorbent sanitary article, characterized in that it comprises the following steps:

providing a first continuous layer (25) of a liquid-permeable, flexable sheet material, providing a second continuous layer (28) of a flexible sheet material which is impermeable to liquids, providing at least one generally rectangular portion of an absorbent structure according to any one of claims 1 to 19, and combining the first continuous layer (25), the second continuous layer (28) and the absorbent structure in a manner such that the absorbent structure is disposed and fixed between the first and second continuous layers (25, 28).

\* \* \* \* \*